United States Patent [19]

Mersch et al.

[11] Patent Number: 5,406,938
[45] Date of Patent: Apr. 18, 1995

[54] GLARE ELIMINATION DEVICE

[75] Inventors: Steven H. Mersch, Germantown; Julia C. Putnam, Cincinnati; Jack B. Stubbs, Waynesville, all of Ohio

[73] Assignee: Ethicon, Inc., Somerville, N.J.

[21] Appl. No.: 936,379

[22] Filed: Aug. 24, 1992

[51] Int. Cl.⁶ .................................. A61B 1/00
[52] U.S. Cl. ....................... 128/4; 359/493; 353/20
[58] Field of Search .................. 128/4; 359/493, 486, 359/487; 353/20

[56] References Cited

U.S. PATENT DOCUMENTS

| 3,567,309 | 3/1971 | Jasgur | 359/493 X |
| 4,759,615 | 7/1988 | Bainbridge et al. | 359/493 |
| 4,808,978 | 2/1989 | Vernay | 359/493 X |
| 4,878,485 | 11/1989 | Adair | 128/4 X |
| 5,193,525 | 3/1993 | Silverstein et al. | 128/4 |
| 5,260,827 | 11/1993 | Dziekan | 359/493 |

FOREIGN PATENT DOCUMENTS 3206412 9/1991 Japan.
4246612 9/1992 Japan.

Primary Examiner—Richard J. Apley
Assistant Examiner—Beverly A. Meindl

[57] ABSTRACT

Apparatus for reducing the glare and enhancing imaging during an endoscopic procedure. The apparatus has a first portion which linerally polarizes illumination in a first direction and a second portion which analyzes the reflected illumination in a direction at 90 degrees to the first direction.

11 Claims, 2 Drawing Sheets

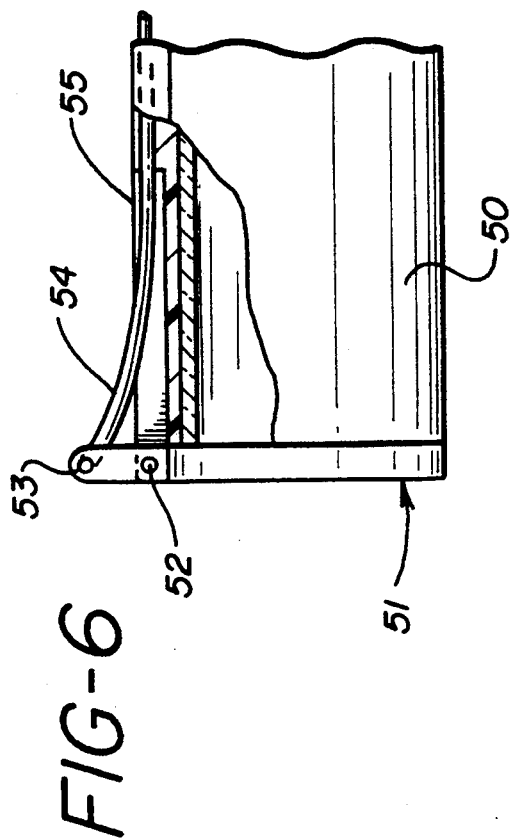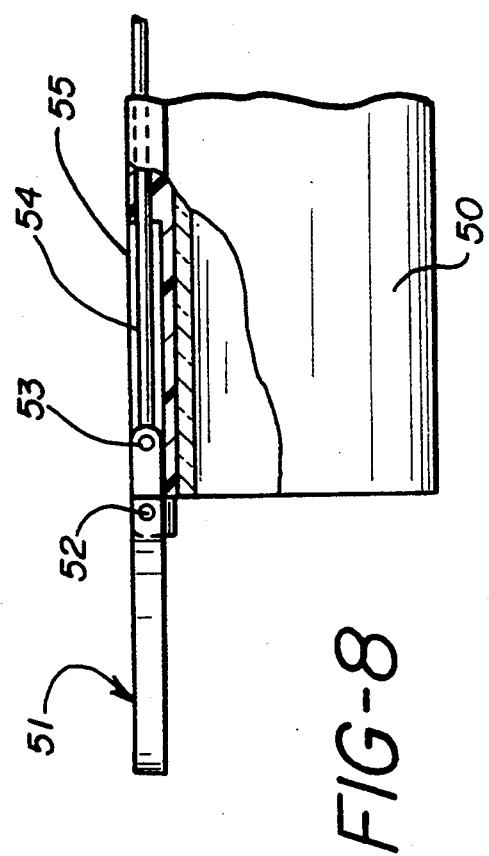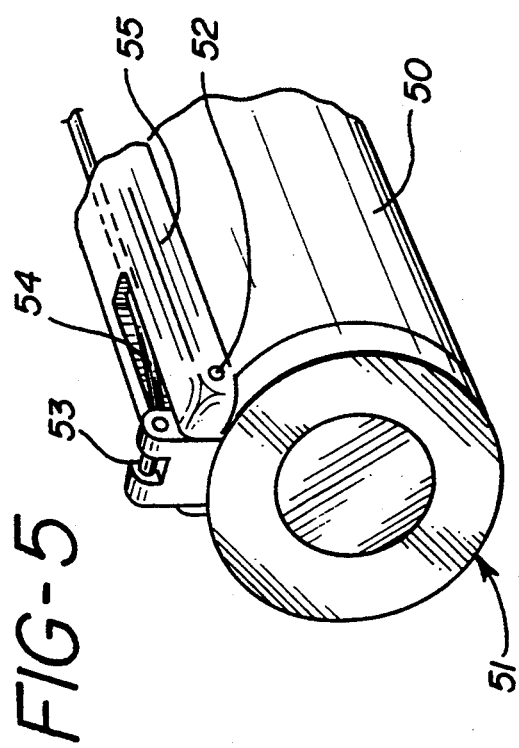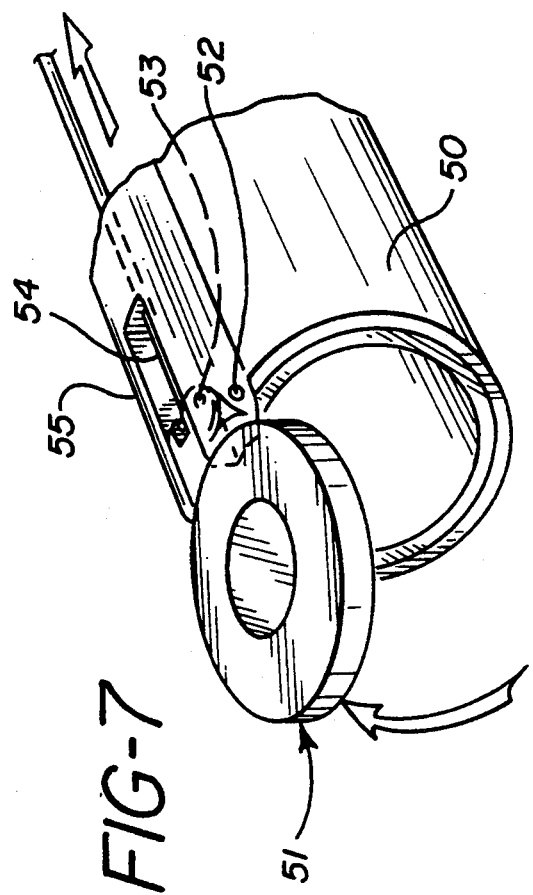

GLARE ELIMINATION DEVICE

FIELD OF INVENTION

This invention relates to methods and sterile devices for use in video assisted minimally invasive surgery, for example, endoscopy, laparoscopy or other optically assisted viewing procedures. More specifically, the invention relates to a sterile device which reduces the glare present when utilizing an endoscope in an endoscopic procedure. The term "endoscopic" as used herein is meant to refer to any surgical procedure using either natural body openings and/or small artificial openings made by puncture or incision; the term "endoscope" as used herein is meant to refer to the viewing devices for an endoscopic procedure.

BACKGROUND OF THE INVENTION

Endoscopic surgery has been gaining wide acceptance as an improved and cost effective technique for conducting certain surgical procedures. In endoscopic surgery, a trocar, which is a pointed piercing device, is inserted into the body with a cannula placed around the trocar. After the trocar pierces the abdominal wall, it is removed and the cannula remains in the body. Through this cannula, endoscopic procedures are possible. Often multiple openings are produced in the body with a trocar so that an endoscopic instrument may be placed in one cannula, appropriate viewing and illuminating means placed in another cannula and so forth. As more is learned about endoscopic surgical procedures and more instruments developed, the type of procedures that may be performed will increase. Presently, some procedures include gall bladder, diagnostic procedures, bowel resection, joint repair, tissue repair, and various sterilization procedures.

An endoscope includes a relatively long tubular member which is placed through a cannula or natural body opening. The tubular member carries fiber optics from an appropriate light source to the end of the tube to provide illumination of the surgical site. The tube also carries imaging means for viewing the surgical site. Many scopes will have the outer annular portion at the end of the tube used for illumination and the central portion of the tube used for imaging. There are also scopes which have one circular area of the tube used for illumination with appropriate fiber optics and an adjacent circular area of the tube used for imaging. Still other scopes may include an open channel in the tube through which one or more small instruments may also be introduced into the surgical site.

In endoscopic procedures, glare often presents a problem and reduces the information in the image being provided to the surgeon during the procedure. Glare may obscure not only the area of interest but also surrounding areas. All of the internal organs reflect light and produce glare due to their wet surfaces. Also, instruments being utilized within the surgical environment will cause glare because of their polished and/or smooth surfaces.

One type of reflection, termed "diffuse" is a scattered reflection from the surface or sub-surface of the illuminated object and contains desirable information. A second type of reflection is what is known as mirrored reflection or "specular" reflection and does not change the nature of the incident or illuminating light. This reflection obscures the image.

Another problem with endoscopes is the difficulty of sterilizing such devices. As these devices are expensive they are used over and over again. They are not sterilized but at the present time and are only disinfected between uses.

It is an object of the present invention to reduce glare present in an endoscopic image. It is another object of the present invention to improve or enhance the image produced during an endoscopic procedure. It is a further object of the present invention to produce a low cost disposable device for use with an endoscope. It is yet a further object of the present invention to provide a device that will allow or provide that the endoscope will be sterile during use.

SUMMARY OF THE PRESENT INVENTION

The present invention provides a method for reducing glare and enhancing visualization during endoscopic procedures. In certain embodiments of the present invention, the diagnostic capabilities of certain endoscopic diagnostic procedures may also be enhanced. In the method of the present invention, the illumination present in an endoscopic procedure is polarized with a first polarizing means or filter and through a second polarizing means or filter the reflected illumination is analyzed. By "polarize" or "polarizing means" it is meant an optical device whose input is natural light and whose output is some form of polarized light. Natural light is electromagnetic radiation with wavelengths between 300 and 1200 nanometers and which contains two or more polarization states. The terms light, illumination and the such are used herein to include, not only visible light, but the entire range of electromagnetic radiation as described above. In the device of the present invention, a first polarizer polarizes light in a first direction. A second polarizer analyzes the reflected illuminations. In certain embodiments of the present invention, the first polarizer linearly polarizes light in a first direction. The second polarizer linearly polarizes light in a direction at 90° to the first direction. Some devices of the present invention comprises a hollow tube with one end of the tube open and the tube sized to fit over the illuminating end of an endoscope. The opposite end of the tube is at least partially closed by polarizers. In a preferred embodiment of the sterile medical device of the present invention, the end of the tube is totally closed with polarizers. The outer annular portion of the closed end of the tube is a polarizer which linearly polarizes light in a first direction while the central portion of the closed end is a polarizer which linearly polarizes light in a direction at 90° to the first direction. The second polarizer which is polarizing the reflected light is often termed an analyzer.

BRIEF DESCRIPTION OF THE DRAWINGS

FIG. 5 is a perspective view of another embodiment of a sterile medical device of the present invention;

FIG. 6 is a cross-sectional view of the device depicted in FIG. 5;

FIG. 7 is a perspective view of the device depicted in FIG. 5 with the polarizer assembly in an open position; and FIG. 8 is a cross-sectional view of the device depicted in FIG. 7.

DETAILED DESCRIPTION OF THE DRAWINGS

Figure 1:
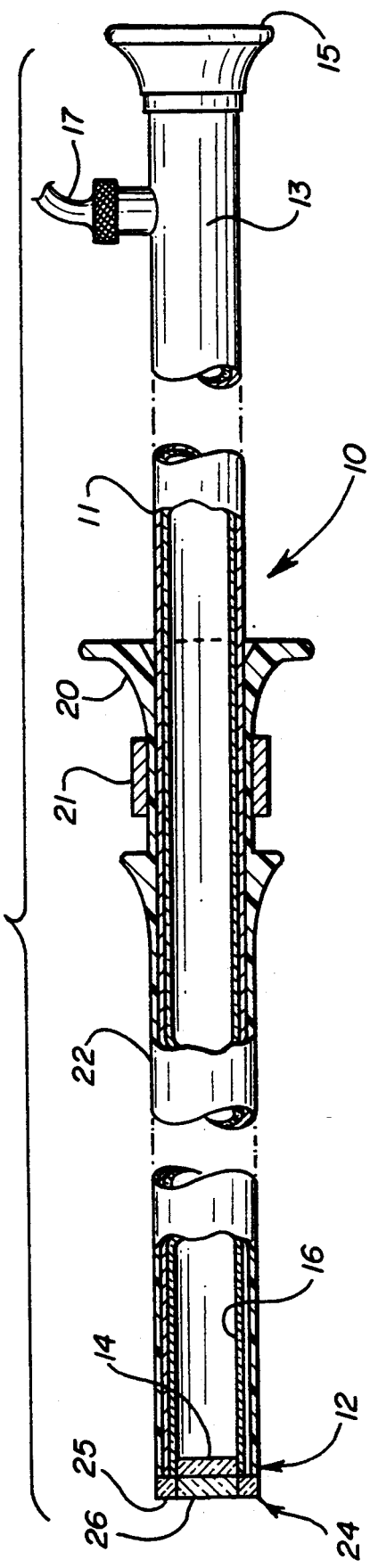
FIG. 1 is a cross-sectional view of a sterile device of the present invention positioned on an endoscope.

Referring to the drawings, in FIG. 1 there is shown an endoscope 10. The endoscope comprises an elongated portion 11 which may be inserted in a cannula, or natural body opening, with the distal end 12, placed in the surgical environment. Through the center of the endoscope is an imaging mechanism 13 which, at the distal end, has an appropriate lens 14 and at the proximal end has a suitable eyepiece 15. In many embodiments, the viewing mechanism is attached to a camera and imaging monitor. The endoscope also comprises illuminating means which, in this embodiment, is fiber optics 16 positioned at the outer periphery of the endoscope around the imaging means. The fiber optics are connected to a suitable light source 17 as is well known in the art.

Figure 2:
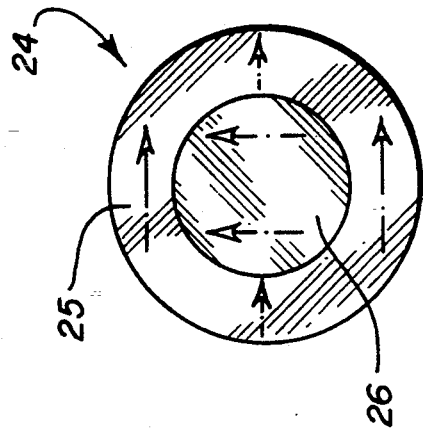
FIG. 2 is an enlarged end view of the device depicted in FIG. 1.

The sterile medical device of the present invention is an elongated hollow tube 22. The tube fits snugly about the endoscope. The open end of the tube has an outwardly tapered portion 20. A ring 21 is mounted on the tube as shown and may be slid over the tapered portion to insure a snug fit of the tube on the endoscope. The tube terminates at the distal end of the endoscope. The distal end of the sterile medical device is the polarizer assembly 24. As more clearly shown in FIG. 2 the polarizer assembly comprises an outer annular portion 25 about the periphery of the assembly which linearly polarizes light in a first direction (in the horizontal direction in this embodiment). The polarizer assembly includes a central analyzer 26 whose polarizing axis is 90° to the first direction (in the vertical direction in this drawing.) If desired, the analyzer, instead of being located at the distal end of the tube, could be located adjacent the eyepiece; or anywhere within the imaging means.

Figure 4:
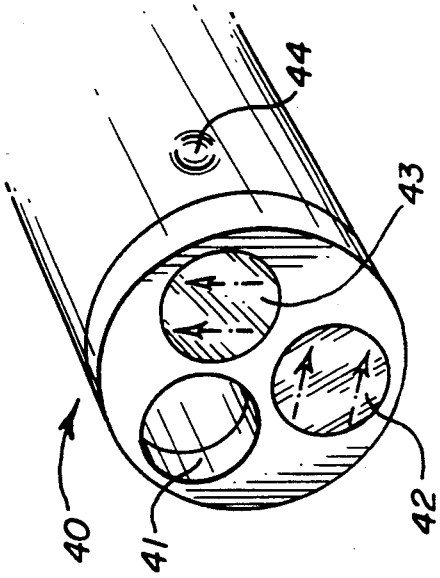
FIG. 4 is a perspective view of another embodiment of a medical device of the present invention.
Figure 3:
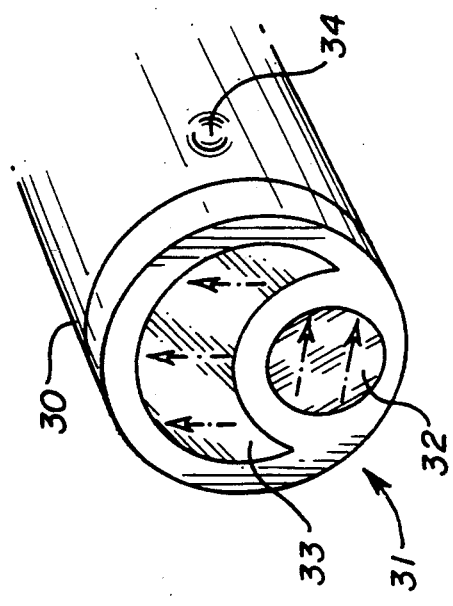
FIG. 3 is a perspective view of an embodiment of a sterile medical device according to the present invention.

Referring to FIG. 3, there is shown another embodiment of a sterile medical device of the present invention. In some endoscopes, the illumination is provided in one channel of the endoscope while the lens or imaging mechanism of the endoscope is provided in an adjacent channel. When utilizing such a endoscope, the sterile medical device of the present invention could be constructed as shown in FIG. 3. The distal portion 30 of the medical device includes a polarizer assembly 31 having a first circular portion 32 which linearly polarizes light in a first direction. An adjacent portion 33 analyzes light in a direction 90° to the first direction. The device would include along its outer periphery a suitable indent 34 or alignment means in order to locate or position the device on the endoscope so that the polarizers align themselves with the light source and the imaging means of the endoscope. Also in some endoscopes, there may be included an open channel. As shown in FIG. 4, a medical device 40 according to the present invention could include an open channel 41. The open channel is used to accept small instruments used in an endoscopic procedure. Adjacent the first channel is a first circular area 42 which linearly polarizes light in the first direction. A second circular area 43 which analyzes light in a direction 90° to the first direction is disposed adjacent said open channel. Again, the medical device would include an indent 44 to appropriately align the device on the endoscope.

The medical device of the present invention may be a tube which covers substantially the entire length of the endoscope and which is attached to the endoscope by suitable coupling means such as shown in FIG. 1. In some embodiments of the present invention, it may be desirable to use a very shortened tube that only fits on the distal end of the endoscope but is sized to fit snugly on that end to avoid inadvertent removal. It is preferred that the tube be a relatively rigid tube for ease of use. A rigid tube is often easier to place on an endoscope and more easily inserted through a cannula or natural body opening.

The material used to make the tubular and coupler portions of the medical devices of the present invention may be any of the standard polymeric or metallic materials used in medical instruments. It is preferred that a material be used that can be easily sterilized; for example, by cobalt irradiation. One such suitable material would be polyethylene. The tubular portion of the medical device will have a length of about 11 inches with an outside diameter of 7/16 of an inch and an inside diameter of 13/32 of an inch so that it will fit a standard 10 mm operative endoscope. The polarizer may be made from polyvinylalcohol laminated in an acrylic resin or other appropriate substrate. The outer annular polarizer for a 10 mm laparoscope would have an outside diameter of about 7/16 of an inch and an inside diameter of ¼ of an inch with a thickness of about 0.01 inch. The inner central polarizer would have a diameter of ¼ of an inch with a thickness of 0.01 inch.

Referring to FIGS. 5 through 8, there is shown another sterile medical device of the present invention. It may be desirable during certain surgical procedures that the illumination not be polarized throughout the entire procedure. The device depicted in FIGS. 5–8 allows the surgeon to polarize or not polarize the illumination as desired. The device shown comprises a hollow tube 50 which is sized to fit snugly over the distal end of an endoscope. The polarizer assembly 51 which closes the distal end of the tube is pivotally mounted on the tube by a hinge 52. Extending from the periphery of the polarizer assembly is a pin 53. An activation rod or wire 54 is attached to the pin and extends through an opening 55 in the tube to the proximal end of the endoscope. As seen in FIGS. 7 and 8, if the surgeon does not desire polarized illumination at some point in the surgical procedure, it is a simple matter to pull the activation rod and pivot the polarizer assembly out of the path of illumination.

While the polarizing assemblies disclosed above provide for linear polarization in different directions, the present invention is not meant to be limited to linear polarization. Polarization may occur in various states; such as linear, circular, elliptical etc. The polarizing assemblies of the present invention polarize the illumination in one state and analyze the reflected illumination in a different polarization state.

While the present invention may have its primary use in reducing glare and enhancing visual representation during endoscopic surgical procedures, it also has use in endoscopic diagnostic procedures. For example, in certain diagnostic procedures that use either infra-red or ultra-violet light, it may be desirable to polarize such light in a given state and then analyze the reflected light with an analyzer that polarizes such light in a different polarization state.

Although this invention has been shown and described with respect to certain embodiments thereof, it should be understood by those skilled in the art that various changes in form and detail may be made without departing from the spirit and scope of the claimed invention.

What is claimed is:

1. A method for reducing glare, enhancing visualization or improving diagnostic capability in an endoscopic procedure comprising:

providing an endoscope comprising an illumination means and a visualization means, said endoscope having a distal end for illuminating a surgical site with said illumination means and for receiving reflected illumination from the surgical site with said visualization means;

providing a sterile medical device adapted to fit over the distal end of the endoscope, said sterile medical device having a distal end including a first polarizing filter which linearly polarizes illumination in a first direction and a second polarizing filter independent of said first polarizing filter which polarizes light in a second direction;

placing the sterile medical device over the distal end of the endoscope so that the distal end of the sterile medical device is adjacent the distal end of the endoscope;

accessing a surgical site by locating the distal end of the endoscope in a body at the surgical site;

which procedure includes both illumination with said illumination means and visualization with said visualization means, and polarizing the illumination with said first polarizing filter in a first linear direction and through said second polarizing filter, analyzing the reflected illumination in a second linear direction.

2. A method according to claim 1 wherein the reflected illumination is polarized in a second linear direction at 90 degrees to said first linear direction.

3. A sterile medical device for use with an endoscope to selectively reduce glare in an endoscopic procedure, said device comprising a hollow tube, one end of said tube being open and the inner diameter of said tube being sized to fit over the illumination end of an endoscope, the opposite end of said tube being a polarizing assembly, said assembly having a first portion which linearly polarizes illumination in a first direction and a second portion which acts independently from said first portion as an analyzer in a second direction at 90 degrees to said first direction.

4. A sterile medical device according to claim 3 wherein the polarizing assembly is pivotally mounted on the end of the tube whereby the assembly may be moved out of the path of illumination.

5. A sterile medical device according to claim 3 wherein the first portion of the polarizing assembly is a circular area which polarizes illumination in said first direction and the second portion is a juxtaposed circular area which analyzes reflected illumination in said second direction.

6. A sterile medical device according to claim 3 wherein the end of the hollow tube opposite the open end is closed by a polarizing assembly, said assembly having an outer annular polarizing area for linearly polarizing illumination in a first direction and an inner circular central area which analyzes reflected illumination in a direction at 90 degrees to said first direction.

7. A sterile medical device according to claim 6 wherein the hollow tube is rigid.

8. A sterile medical device for use with an endoscope in an endoscopic procedure, said endoscope having illuminating means and visualization means, said device comprising means for polarizing the illumination in a first polarization state and analyzing means for polarizing state different than said first polarization state, wherein said analyzing means is independent of said means for polarizing the illumination, and wherein said means for polarizing and said analyzing means are arranged to selectively reduce glare and enhance visualization during the endoscopic procedure.

9. A device according to claim 8 wherein the means for polarizing the illumination is a linear polarization means.

10. A device according to claim 8 wherein the analyzing means is a linear polarization means.

11. A device according to claim 8 wherein the means for polarizing the illumination is a linear polarization means that polarizes light in a first direction and the analyzing means is a linear polarization means that polarizes light at 90 degrees to said first direction.

* * * * *